US010952432B2

(12) United States Patent
Aeschbach

(10) Patent No.: US 10,952,432 B2
(45) Date of Patent: Mar. 23, 2021

(54) CANNABIDIOL COMPOSITIONS AND USES THEREOF

(71) Applicant: PHARMOTECH SA, Plan les Ouates (CH)

(72) Inventor: Rodin Aeschbach, Meyrin (CH)

(73) Assignee: PHARMOTECH SA, Plan les Ouates (CH)

( * ) Notice: Subject to any disclaimer, the term of this patent is extended or adjusted under 35 U.S.C. 154(b) by 32 days.

(21) Appl. No.: 16/306,219

(22) PCT Filed: Jun. 1, 2017

(86) PCT No.: PCT/EP2017/063385
§ 371 (c)(1),
(2) Date: Nov. 30, 2018

(87) PCT Pub. No.: WO2017/207730
PCT Pub. Date: Dec. 7, 2017

(65) Prior Publication Data
US 2019/0297882 A1    Oct. 3, 2019

(30) Foreign Application Priority Data

Jun. 2, 2016 (EP) .................................... 16172574

(51) Int. Cl.
| | |
|---|---|
| *A61K 31/05* | (2006.01) |
| *A01N 31/16* | (2006.01) |
| *A61L 2/00* | (2006.01) |
| *A61L 2/18* | (2006.01) |
| *A61L 2/23* | (2006.01) |
| *D21H 21/36* | (2006.01) |
| *A61K 8/34* | (2006.01) |
| *A23L 33/105* | (2016.01) |
| *C11D 3/38* | (2006.01) |
| *A61L 29/16* | (2006.01) |
| *A23K 20/111* | (2016.01) |
| *A61L 31/16* | (2006.01) |
| *C11D 3/48* | (2006.01) |
| *A61K 31/352* | (2006.01) |
| *A61L 27/54* | (2006.01) |
| *A61L 31/10* | (2006.01) |
| *A61Q 17/00* | (2006.01) |
| *D21H 25/00* | (2006.01) |
| *A61L 29/08* | (2006.01) |

(52) U.S. Cl.
CPC ............ *A01N 31/16* (2013.01); *A23K 20/111* (2016.05); *A23L 33/105* (2016.08); *A61K 8/347* (2013.01); *A61K 31/05* (2013.01); *A61K 31/352* (2013.01); *A61L 2/0082* (2013.01); *A61L 2/18* (2013.01); *A61L 2/23* (2013.01); *A61L 27/54* (2013.01); *A61L 29/085* (2013.01); *A61L 29/16* (2013.01); *A61L 31/10* (2013.01); *A61L 31/16* (2013.01); *A61Q 17/005* (2013.01); *C11D 3/381* (2013.01); *C11D 3/48* (2013.01); *D21H 21/36* (2013.01); *D21H 25/00* (2013.01); *A61L 2202/24* (2013.01); *A61L 2202/25* (2013.01); *A61L 2300/404* (2013.01)

(58) Field of Classification Search
CPC .............................. A61K 31/352; A61K 31/05
See application file for complete search history.

(56) References Cited

U.S. PATENT DOCUMENTS

| | | | |
|---|---|---|---|
| 7,799,782 B2 * | 9/2010 | Munson ............... | C07D 405/12 514/234.5 |
| 2013/0203715 A1 | 8/2013 | Hava et al. | |
| 2015/0086494 A1 * | 3/2015 | Sekura ................ | A61K 9/0014 424/59 |

FOREIGN PATENT DOCUMENTS

FR    2965477    4/2012

OTHER PUBLICATIONS

Dahiya et al. CAS: 91: 14478, 1979.*
Dahiya et al., Indian Drugs & Pharmaceuticals Industry, 1977, 12(4): 31-4 (abstract).*
Appendino et al., J. of Natural Products, 2008, 71(8): 1427-1430.*
Appendino, G. et al. "Antibacterial Cannabinoids from *Cannabis sativa*: A Structure—Activity Study" J. Nat. Prod., 2008, pp. 1427-1430, vol. 71.
Ashton, C. H. "Pharmacology and effects of cannabis: a brief review" *British Journal of Psychiatry*, 2001, pp. 101-106, vol. 178.
Barbeau, J. et al. Multiparametric Analysis of Waterline Contamination in Dental Units *Applied and Environmental Microbiology*, Nov. 1996, pp. 3954-3959, vol. 62, No. 11.
Bone, R. C. et al. "Definitions for Sepsis and Organ Failure and Guidelines for the Use of Innovative Therapies in Sepsis" *Chest*, Jun. 1992, pp. 1644-1655, vol. 101, No. 6.
File, T. M. et al. "An Outbreak of *Pseudomonas aeruginosa* Ventilator-Associated Respiratory Infections Due to Contaminated Food Coloring Dye—Further Evidence of the Significance of Gastric Colonization Preceding Nosocomial Pneumonia" *Concise Communications*, Jul. 1995, pp. 417-418, vol. 16, No. 7.
Juhas, M. et al. "Quorum sensing: the power of cooperation in the world of Pseudomonas" *Environmental Microbiology*, 2005, pp. 459-471, vol. 7, No. 4.

(Continued)

*Primary Examiner* — Rei Tsang Shiao
(74) *Attorney, Agent, or Firm* — Saliwanchik, Lloyd & Eisenschenk

(57) ABSTRACT

The present invention is directed to use of cannabidiol and compositions thereof as an anti-bacterial agent against multi-drug resistant bacteria such as *Pseudomonas aeruginosa*.

4 Claims, 1 Drawing Sheet
Specification includes a Sequence Listing.

(56) References Cited

OTHER PUBLICATIONS

Markou, P. et al. "Pathogenesis of intestinal *Pseudomonas aeruginosa* infection in patients with cancer" *Frontiers in Cellular and Infection Microbiology*, Jan. 7, 2014, pp. 1-5, vol. 3, Article 115.
Masak, J. et al. "*Pseudomonas* biofilms: possibilities of their control" *FEMS Microbiol Ecol*, 2014, pp. 1-14, vol. 89.
Rybtke, M. et al. "*Pseudomonas aeruginosa* Biofilm Infections: Community Structure, Antimicrobial Tolerance and Immune Response" *J. Mol Biol*, 2015, pp. 3628-3645, vol. 427.
Wong, S. etal. "Recalls of Foods and Cosmetics Due to Microbial Contamination Reported to the U.S. Food and Drug Administration" *Journal of Food Protection*, 2000, pp. 1113-1116, vol. 63, No. 8.
Written Opinion in International Application No. PCT/EP2017/063385, dated Oct. 20, 2017, pp. 1-12.

\* cited by examiner

CANNABIDIOL COMPOSITIONS AND USES THEREOF

CROSS-REFERENCE TO RELATED APPLICATION

This application is the U.S. national stage application of International Patent Application No. PCT/EP2017/063385, filed Jun. 1, 2017.

The Sequence Listing for this application is labeled "Seq-List.txt" which was created on Nov. 26, 2018 and is 3 KB. The entire content of the sequence listing is incorporated herein by reference in its entirety.

FIELD OF THE INVENTION

The present invention relates to the field of antibacterial agents. In particular, the invention relates to the use of cannabinoid compositions as anti-bacterial agent against multi-drug resistant bacteria.

BACKGROUND OF THE INVENTION

Biofilm is a structured microbial community which is a naturally occurring form of growth of many microorganisms. Biofilm formation is often a very rapid process, which includes several phases and involves conditioning the carrier surface for enabling the initial binding of the cells to the carrier surface through physicochemical interaction, production of binding molecules (e.g. extracellular polymeric substances, adhesins) for irreversibly anchoring the cells on the carrier surface, organizing the cell community in the form of microcolonies and formation and maturation of the biofilm architecture (Masák et al., 2014, *FEMS Microbiol. Ecol.*, 89: 1-14). Those steps imply significant changes in the physiology of the cells often is leading to changes in cell phenotype, the development of new metabolic pathways and the expression of virulence factors. The deployment of such changes in a unified and coordinated manner between the cells within the colony is achieved through signaling pathways between cells. In the pseudomonads, and in particular the common gram-negative bacterium opportunistic human pathogen, *Pseudomonas aeruginosa*, which is involved in nosocomial and life-threatening infections of immunodepressed patients, this cell-to-cell communication is realized through a chemically-based communication system called Quorum Sensing (QS). QS was shown to be essential to control the initial host defense and the launch of the virulent offensive to the host through the coordination of the timely expression of a battery of virulence factors with the growth of the colony and therefore with the biofilm formation process (Masák et al., 2014, supra; Juhas et al., 2005, *Environmental Microbiology*, 7(4): 459-471). Further, in *Pseudomonas* species, biofilm growth generally increases their resistance to various negative environmental influences since they are metabolically less active within the biofilm and hence less receptive to antimicrobial agents and environmental disruptions. In addition, biofilms form a physical barrier against the entry of antimicrobial agents. Therefore, this increased resistance enables them to inhabit a broad range of niches and colonize the soil matrix, plant tissue, etc. (Masák et al., 2014, supra; Rybtke et al., 2015, *J. Mol. Biol.* 427: 3628-3645). Infections caused by bacterial biofilms of multi-drug resistant (MDR) bacteria, also called nosocomial infections, have become a major concern for most hospitals and healthcare facilities, since they contribute to an increase in morbidity and mortality compared to the underlying diseases alone and impact length of patients' stay and related healthcare costs. Biofilms have been shown to be the underlying cause of many tissue-associated and implant-associated infections (Rybtke et al., 2015, supra), such as dental and buccal infections such as dental caries, periodontitis, otorhinolaryngologic infections such as otitis, in particular chronic otitis media (COM) and chronic sinusitis, respiratory infections such as cystic fibrosis (CF) and pneumonia, especially pneumonia in mechanically ventilated patients, skin infection such as chronic wound infections, musculoskeletal infections, urological and/or prostatic track infections, biliary tract infection, native valve endocarditis, opportunistic infections in immunodepressed patients such as cancer patients (Markou et al., 2014, *Frontiers in Cellular and infection microbiology*, 3(115), 1-5) and a range of medical device-related infections. Treatment of infections produced by *P. aeruginosa* is complicated by the organism's is resistance profile and may lead to treatment failure and/or exposing patients to adverse effects from antibiotic drug regimens. Current medications for preventing and treating those nosocomial infections are extensive antibiotherapy, which however often develops into lethal infections due to the high resistance of the bacteria to many antibiotics and their shielding by biofilms that protect it from the action of both drugs and immune system. Specifically, acute fulminant infections, such as bacteremic pneumonia, sepsis, burn wound infections and meningitis are associated with extremely high mortality.

Further, bacteria biofilm formation constitutes a problem in food and cosmetic formulation contamination (Wong et al., 2000, *Journal of Food protection*, 8, 1015-1153), artwork degradation, water contamination (Barbeau et al., 1996, *Appl. Environ. Microbiol.*, 62(11), 3954-3959) and medical devices contamination (File et al., 1995, 16(7), 417-418).

Various approaches have been developed to regulate/suppress *Pseudomonas* biofilm and formation thereof, which may or may not include interfering with the regulatory mechanisms of biofilm formation. Quorum sensing, due to its involvement in the expression of several virulence factors and biofilm formation in *P. aeruginosa* has been an attractive target for the design of novel drugs for the treatment of *P. aeruginosa* infections (Juhas et al., 2005, supra). Some substances have been presented as being able to interfere with the mechanism of quorum sensing (QS) such as water extracts of rhubarb, *Fructus gardeniae* and *Andrographis paniculata*, cis-2-Dodecenoic acid, garlic, other aqueous extracts of common fruits, herbs, and spices, resveratrol, erythromycin, azithromycin, clarithromycin and spiramycin (Masák et al., 2014, supra). However, none of the currently developed quorum sensing inhibitors has a universal utilization and may require an appropriate approach depending on the site where the biofilm is formed (Masák et al., 2014, supra).

Cannabidiol (CBD) is a type of cannabinoid found as a major constituent of the *cannabis* plant, especially *Canabis sativa* (Asthton, 2001, *British Journal of Psychiatry*, 178, 101-106). CBD has been described as a non-psychoactive substance having potential medical applications in the treatment of disorders such as epilepsy, multiple sclerosis spasms, anxiety disorders, schizophrenia, nausea, convulsion and inflammation, as well as inhibiting cancer cell growth. CBD, pre-CBD as well as the synthetic abnormal CBD (abn-CBD) have been described as having activity against a variety of methicillin-resistant *Staphylococcus aureus* (MRSA) strains (Appendino et al., 2008, *J. Nat. Prod.*, 71: 1427-1430).

Due to the severity of infections and contaminations due to Gram-negative bacteria such as *P. aeruginosa*, the increasing resistance of those bacteria to current antibiotic medications and the high risk of some patients to catch such infections, it would be highly desirable to have new methods for preventing and/or treating Gram-negative bacteria related infections, such as nosocomial infections.

SUMMARY OF THE INVENTION

The present invention relates to the unexpected finding that cannabidiol (CBD) is active against a multi-drug resistant bacteria Gram-negative bacteria, *P. aeruginosa* bacteria, and thus can be useful for preventing or decreasing the extent of the virulence of this bacteria for example by inhibiting the biofilm formation and the production of virulence factors. Therefore, CBD can provide an effective agent for prevention and/or treatment of infections or contaminations caused by bacterial biofilm forming multi-drug resistant bacteria.

An aspect of the invention provides CBD or a composition thereof for use as a selective antibacterial agent against *P. aeruginosa*, in particular as an inhibitor of biofilm formation by the said bacteria.

Another aspect of the invention relates to CBD or a composition thereof for use in the prevention and/or treatment of a disease caused by *P. aeruginosa* bacteria, in particular in the prevention and/or treatment of a disease or disorder selected from the group consisting of hospital-acquired infection, respiratory tract infections, skin and soft tissue infections, wound infections, dental and buccal infections, otorhinolaryngologic infections, urological and/or prostatic track infections, gastrointestinal infections, biliary tract infection, eye infections, bacteremia, sepsis, central nervous system infections and endocarditis.

An aspect of the invention provides a use of CBD or a composition thereof for the preparation of a pharmaceutical preparation for the prevention and/or treatment of a disease caused by *P. aeruginosa* bacteria, in particular in the prevention and/or treatment of a disease or disorder selected from the group consisting of hospital-acquired infection, respiratory tract infections, skin and soft tissue infections, wound infections, dental and buccal infections, otorhinolaryngologic infections, urological and/or prostatic track infections, gastrointestinal infections, biliary tract infection, eye infections, bacteremia, sepsis, central nervous system infections and endocarditis.

Another aspect of the invention relates to the use of CBD, or a composition thereof as a sterilizing and/or decontamination agent, in particular as a sterilizing and/or decontamination agent for medical material, rooms intended for medical, aesthetic or hygiene practice or for preparations intended for human or veterinary use.

In a particular embodiment, is provided a use of CBD or a composition thereof for conservation of work of art.

Another aspect of the invention relates to a decontaminating composition comprising CBD, in particular comprising CBD at a concentration between about 0.1 µg/mL to 200 mg/mL, for example from about 0.1 µg/mL to 1 mg/mL, in particular from 0.1 µg/mL to 50 µg/mL, more particularly from 1 µg/mL to 50 µg/mL and a further physiologically acceptable carrier, diluent or excipient.

Another aspect of the invention relates to a sterilizing composition comprising CBD, in particular comprising CBD at a concentration between about 0.1 µg/mL to 200 mg/mL, for example from about 0.1 µg/mL to 1 mg/mL, in particular from 0.1 µg/mL to 50 µg/mL, more particularly from 1 µg/mL to 50 µg/mL and a further physiologically acceptable carrier, diluent or excipient.

Another aspect of the invention relates to a food, beverage or a cosmetic preparation comprising CBD or a decontaminating composition according to the invention.

Another aspect of the invention relates to an article coated with CBD or a composition thereof, in particular an article for use in medical, aesthetic or hygiene practice or in contact with preparations intended for human or veterinary use.

According to another aspect of the invention, is provided a kit for decontamination (e.g. of material surfaces or solutions) or sterilizing comprising CBD a composition thereof according to the invention, and optionally instructions for use.

Another aspect of the invention relates a method of sterilisation and/or decontamination of medical material, rooms intended for medical, aesthetic or hygiene practice or preparations intended for human or veterinary use comprising the step of contacting said material, rooms or preparations with CBD, or a composition thereof, in particular with CBD, or a composition thereof, at a concentration between about 0.1 µg/mL to 200 mg/mL.

According to another aspect, is provided a method of preventing or inhibiting *P. aeruginosa* virulence or the formation of a biofilm thereof, said method comprising contacting a surface or a tissue susceptible to be contaminated by *P. aeruginosa* bacteria with CBD, or a composition thereof, in particular with CBD, or a composition thereof, at a concentration between about 0.1 µg/mL to 200 mg/mL.

According to another aspect, is provided a method of inhibiting virulence of *P. aeruginosa* bacteria and/or biofilm formation by said bacteria, in particular an ex vivo method, said method comprising the step of contacting a material or a solution containing said bacteria and/or biofilm thereof with CBD, or a composition thereof.

Another aspect of the invention relates to a method for preventing and/or treating of a disease caused by *P. aeruginosa* bacteria, in particular a disease or disorder selected from the group consisting of hospital-acquired infection, respiratory tract infections, skin and soft tissue infections, wound infections, dental and buccal infections, otorhinolaryngologic infections, urological and/or prostatic track infections, gastrointestinal infections, biliary tract infection, eye infections, bacteremia, sepsis, central nervous system infections and endocarditis, said method comprising administering a therapeutically effective amount of CBD, or a composition thereof according to the invention, to a subject in need thereof, in particular where CBD, or a composition thereof is at a concentration between about 0.1 µg/mL to 200 mg/mL, for example from about 0.1 µg/mL to 1 mg/mL, in particular from 0.1 µg/mL to 50 µg/mL, more particularly from 1 µg/mL to 50 µg/mL.

Another aspect of the invention relates a method for conservation of work of art, such as paintings and antique manuscripts, comprising the step of contacting said work of art with CBD, or a composition thereof.

DETAILED DESCRIPTION OF THE INVENTION

Figure 1:
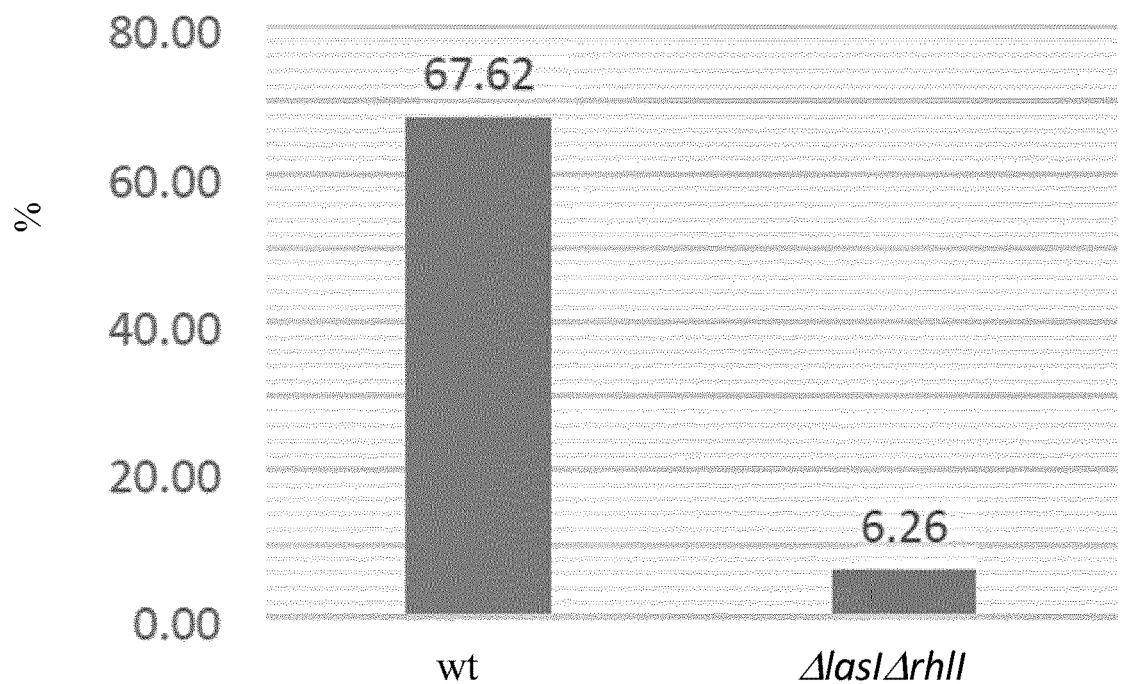
FIG. 1 shows the relative elastase enzymatic activity of eleastase produced by *P. aeruginosa* PAOW1(PT5) (wt) incubated in the presence of CBD at 500 µg/ml as described in Example 2 compared to the enzymatic activity of elastase from the wt or from the wt or from *P. aeruginosa* ΔlasIΔrhlI mutant in absence of CBD.

The term "hospital-acquired infection (HAI)" or "nosocomial infection" refers to an infection that is contracted from the environment or staff of a healthcare facility (e.g. hospital, nursing home, rehabilitation facility, clinics). Main routes of infection spread comprise contact transmissions (e.g. during patient-care activities that require direct personal contact, contaminated instruments, needles, gloves or dressings), droplet or airborne transmissions, common vehicle transmission (e.g. contaminated food, water, medications, devices and equipment). In some cases, the microorganism originates from the patient's own skin or gut microbiota, becoming opportunistic after surgery or other procedures that compromise the protective skin or gut barrier, and although the patient may have contracted the infection from their own skin or gut, the infection is considered nosocomial as it develops in the health care setting.

The term "virulence factors" are molecules produced by bacteria that contribute to the pathogenicity thereof such as adhesins, invasins and antiphagocytic factors for colonization of the host or toxins, hemolysins and proteases, which damage the host.

The term "biofilm", as used herein, refers to a structured group of microorganisms in which cells adhere to each other and often these cells adhere to a surface. *P. aeruginosa*, like some other gram-negative bacteria, grows in the form of aggregates called structured biofilms wherein the cells are coated with a complex matrix composed of extracellular polymers.

The term "quorum sensing (QS)" refers to a mechanism leading to a regulation of gene expression in response to fluctuations in cell-population density. Quorum sensing bacteria produce and release chemical signal molecules (autoinducers) that increase in concentration as a function of cell density and a detection of a threshold stimulatory concentration of an autoinducer leads to an alteration in gene expression. A variety of different molecules can be found as signals and include oligopeptides N-Acyl Homoserine Lactones (AHL) and a family of autoinducers known as auto-inducer-2 (AI-2) in gram-negative bacteria. Quorum sensing can occur within a single bacterial species as well as between diverse species. Bacteria use quorum sensing communication circuits to regulate a diverse array of physiological activities and these include symbiosis, virulence, competence, conjugation, antibiotic production, motility, sporulation, and biofilm formation. *Pseudomonas aeruginosa* possesses two known quorum sensing systems based on acyl homoserine lactone (AHL) molecules that are the las system and the rhl system and a quinolone-based system. The las system consists of the transcriptional activator LasR and the AHL synthase LasI, which directs the synthesis of N-3-oxo-dodecanoyl-homoserine lactone (3-oxo-$C_{12}$-HSL). The rhl system consists of the transcriptional regulator RhlR and the AHL synthase RhlI, which directs the synthesis of N-butanoyl-homoserine lactone ($C_4$—HSL). The las system is considered as a key factor in the maturation and differentiation of biofilm, and the rhl system is responsible for the production of biosurfactants (rhamnolipids) that are necessary for maintaining an open channel system in *Pseudomonas* biofilm. Further, quinolone-based system is based on a signaling molecule 2-heptyl-3-hydroxy-4-(1H)-quinolone (referred to as *Pseudomonas* quinolone signal) (Juhas et al., 2005, supra; Masák et al., 2014, supra).

The term "quorum sensing inhibition" refers to inhibition or attenuation of the process of quorum sensing. The inhibitory activity of agents of the virulence of bacteria via an action on the quorum sensing mechanism can be for example assessed indirectly by their effect on biofilm formation (e.g. by measuring read outs of the biofilm mass such as staining, DNA-quantification confocal laser scanning microscopy to analyze the morphology of the biofilm) or more directly on the quorum sensing signalling components such as by quantification of mRNA levels of genes involved in the quorum sensing signaling and virulence factors (e.g. assays for AHL (N-Acyl Homoserine Lactones) production, QS gene activity, virulence factor production (Las A, LasB, and pyoverdin) and growth curve studies and Bradford assay).

Examples of substances acting as a quorum sensing inhibitor include agents that decrease the production of signaling molecules or inhibiting receptors thereof.

The term "antiseptic compound" refers to a substance that inhibits the growth and the development of microorganisms.

The term "sterilization" refers to the process of elimination of microbiological organisms to achieve asepsis (a sterile microbial environment).

The term "decontamination" refers to the process of cleansing an object or substance to remove contaminants comprising bacteria in order to prevent the spread of bacteria.

The term "contamination" of a surface material, a room surface (e.g. walls, floor or room furniture) or sample preparation (e.g. culture medium, buffer solutions, solubilizing medium, cosmetic, pharmaceutical or food industrial preparations), refers to the presence of bacteria on those surfaces or within those preparations at a level that is considered to be harmful for the user of such material or sample preparation either by topical contact, intubation or ingestion. Food or meal preparations, cosmetic preparation or water can be contaminated with *Pseudomonas aeruginosa* which can rapidly develop within nurturing environment (48 h) and cause for example aerobic food degradation.

The term "medical material", as defined herewith, is any material or piece of equipment used in healthcare such as in surgery or intensive care (such as textile for healthcare, paint in healthcare venue, tubings, etc.) piece of equipment designed to aid diagnosis, monitoring or treatment of medical conditions material. It includes catheters (such as peritoneal dialysis catheters and intravenous catheters), foreign-body implants (such as prosthetic heart valves, cardiac pacemakers, total joint prostheses, renal dialysis shunts), medical imaging machines (such as ultrasound and MRI machines, PET and CT scanners, and x-ray machines), treatment equipment (such as infusion pumps, medical lasers, surgical machines), life support equipment (such as medical ventilators, anesthetic machines, heart-lung machines, ECMO, and dialysis machines), medical monitors (such as displaying ECG, EEG, and blood pressure), medical laboratory equipment (such as for analysis of blood, urine, genes, and dissolved gases in the blood), diagnostic equipment, therapeutic equipment (such as physical therapy machines), dental equipment (such as dental burs) and contact lenses.

The term "room intended for medical, aesthetic or hygiene practice" encompasses any room where a medical, aesthetic or hygiene act will be performed on a subject or on sample or material preparation and where a certain degree of asepsis or hygiene is required. Those rooms encompass clean rooms (e.g. medicament, cosmetics or food conditioning rooms), consulting rooms, delivery rooms, emergency rooms, an intensive care unit rooms, maternity wards, nurseries, sickrooms, padded cells, dentist treatment rooms and operating rooms, aesthetic studios, tanning salons and the like.

The term "respiratory tract infections (or diseases)" are generally defined herewith as infectious diseases caused by bacteria, and in particular a bacteria biofilm, which are involving the respiratory tract and can be classified as upper respiratory tract infections (URI) or lower respiratory tract infection (LRI). Non-limitative examples of respiratory tract infections which can be caused by *Pseudomonas aeruginosa* include pneumonia, bilateral pneumonia with the presence of micro-abscesses and tissue necrosis. The term includes all respiratory tract infections that may occur in patients with cystic fibrosis, patients where previously broad-spectrum antibiotic treatment was used, patients where ventilation support equipment is/was used (such as intubation), immuno-compromised patients, patients with prior conditions such as chronic lung disease, AIDS or blood cancer (blood cancer patients mostly develop respiratory tract infections after receiving drugs), patients with a failure of functioning of the heart pump.

The term "skin and soft tissue infections (or diseases)" are generally defined herewith as infections or diseases that involve bacterial invasion of the skin and underlying soft tissues. Examples of skin infections or diseases caused by *P. aeruginosa* include pyoderma, baby's and children's pyoderma, gangrene (such as gangrene of the extremities, perineum, face and upper part of the pharynx), diffuse rash accompanied by vesicles or papules and ecthyma gangrenosum (EG). The term includes all skin infections in subjects with severe burns leading to tissue necrosis, in subjects after trauma, after skin abrasion (such as scratch and depilation), after contact with contaminated water (such as in steam rooms, jacuzzis and swimming pools), in bedridden subjects and skin inflammation due to skin infection (infective dermatitis). Predisposing factors to skin infection include trauma, pre-existing skin disease, poor hygiene, impaired host immunity (such as leukopenia), and previous treatment with broad-spectrum antibiotic.

The term "wound infections" and "chronic wound infection" includes infections such as surgical wound infection, athlete's foot, gram negative folliculitis, chronic paronychia (green nail syndrome), spa pool folliculitis and ecthyma gangrenosum.

The term "urological and/or prostatic track infections" include urinary tract infections such as ecthyma and chronic bacterial prostatitis. Those may occur in subjects after surgeries, for example in patients with a urinary catheter, or with a disorder of the prostate, or with any urinary tract obstruction or with an anatomical defect of the urinary tract and in paraplegic patients.

The term "dental and buccal infections" includes dental caries and periodontitis.

The term "otorhinolaryngologic infections" includes ear infections such as otitis externa, which involves the outer ear and ear canal, otitis media, which involves the middle ear and otitis interna (otitis labyrinthitis) and chronic sinusitis. Predisposing factors to development of otitis externa include diabetes and advanced age.

The term "eye infections (or diseases)" includes infections after eye trauma or after eye contact with contaminated water or contact lenses.

The term "gastrointestinal infections" include biliary tract infection.

The term "bacteremia" refers to the presence of viable bacteria in the blood stream and may occur in subjects with neutropenia, diabetes, burns, malignant hematological diseases and ecthyma gangrenosum.

The term "sepsis" refers to complication of an infection that is a potentially serious medical condition characterized by a whole-body inflammatory state (called a systemic inflammatory response syndrome or SIRS) and the presence of either a proven (on the basis of sampling or radiology) or probable (considering the patient's clinical presentation, white cell count, CRP, radiology) infection. The term sepsis summarizes clinical pictures, for which, as a rule, fever, leucocytosis, consciousness changes, a hyperdynamic circulation ("warm shock"), and a hyper-metabolic status, mainly as a consequence of the invasion of the normally sterile tissue by microorganisms, are observed. The term sepsis corresponds to the definition of sepsis as defined in the "Definitions for Sepsis and Organ Failure and Guidelines for the Use of Innovative Therapies in Sepsis" from the ACCP/SCCM consensus conference committee (Bone et al., *Chest* 1992, 101, 1644-1655).

The term "central nervous system (CNS) infections (or diseases)" includes all CNS infections which may occur in subjects after head trauma, surgery and procedures involving gaining access to CNS such as lumbar puncture or spinal anesthesia. Predisposing factors to development of CNS infections include pre-existing infection, pre-existing disease (such as head and neck cancer), impaired immune system and advanced age.

The term "endocarditis" or "infective endocarditis (IC)" refers to an inflammation of the inner layer of the heart, the endocardium, which can also involve the heart valves, the interventricular septum, the chordae tendineae, the mural endocardium, or the surfaces of intracardiac devices.

The term "subject" as used herein refers to mammals. For example, mammals contemplated by the present invention include human, primates, domesticated animals such as dogs, cats, cattle, sheep, pigs, horses, laboratory rodents and the like.

As used herein, "treatment" and "treating" and the like generally mean obtaining a desired pharmacological and physiological effect. The effect may be prophylactic in terms of preventing or partially preventing a bacterial infection or a disease, symptom or condition thereof and/or may be therapeutic in terms of a partial or complete cure of a bacterial infection, a disease, condition, symptom or adverse effect attributed to the bacterial infection.

The term "efficacy" of a treatment or method according to the invention can be measured based on changes in the course of infection, disease or condition in response to a use of a compound or a method according to the invention. For example, the efficacy of a treatment or method according to the invention can be measured by its impact on signs or symptoms of infection. A response is achieved when the patient experiences partial or total alleviation, or reduction of unwanted symptoms of infection.

According to one aspect, the efficacy of a treatment according to the invention can be assessed by the effect of an effective amount of CBD on the virulence of *P. aeruginosa* such as an effect on the production of virulence factors, on the biofilm formation and/or the quorum sensing system of the bacteria. According to a particular aspect, the efficacy of a treatment according to the invention can be assayed by the effect (inhibition/decrease) of the quorum sensing cascade of the bacteria, without necessarily killing it.

The term "effective amount" as used herein refers to an amount of CBD, or a formulation thereof that elicits a detectable reduction of the symptoms of the disease in a subject that is being administered said compound or formulation.

Compounds According to the Invention

The term "cannabidiol (CBD)" refers to a type of cannabinoid that can be found in *cannabis* plant having the following chemical structure:

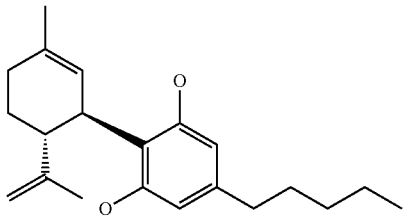 [SMILES: C=C(C)[C@@H]1CCC(C)=C[C@H]1c1c(O)cc(CCCCC)cc1O]

2-[(1R,6R)-6-isopropenyl-3-methylcyclohex-2-en-1-yl]-5-pentylbenzene-1,3-diol, also named s $\Delta^2$-cannabidiol.

It is a major constituent of the *Cannabis* plant, second to THC, and represents up to 40% in its extracts. Compared with THC has a very low affinity for CB1 and CB2 receptors which results in this substance being non-psychoactive. CBD can be extracted from various *Cannabis* plant species including *Cannabis sativa, indica* and *ruderalis*. In particular, CBD can be extracted as a pure compound from genetically modified *cannabis* plant which is producing increased levels of CBD as compared to naturally occurring plants.

According to one embodiment, is provided a CBD of a natural origin, that is extracted from *Cannabis* strains variety.

According to another embodiment, a CBD can be isolated by standard methods known to the skilled person, for example comprising collecting of plant material and extraction and purification.

Alternatively, CBD may be prepared by synthetic methods.

Methods and Uses According to the Invention

According to a particular embodiment, are provided CBD or a composition thereof for use in the prevention and/or treatment of a disease caused by *P. aeruginosa* bacteria.

In a particular embodiment, the provided CBD or compositions thereof are useful as an inhibitor of *Pseudomonas aeruginosa* bacteria.

In a particular embodiment, the provided CBD or compositions thereof are useful as an inhibitor of biofilm formation by *Pseudomonas aeruginosa* bacteria.

In a more particular embodiment, the provided CBD or compositions thereof can be useful in the inhibition or decrease of the virulence of *Pseudomonas aeruginosa* bacteria.

In another particular embodiment, the provided CBD or compositions thereof can be useful as inhibitors of quorum sensing, in particular of the production of virulence factors.

Another particular embodiment provides CBD or a composition thereof for use in the prevention and/or treatment of a hospital-acquired infection caused by *P. aeruginosa*.

Another embodiment provides CBD or a composition thereof for use in the prevention and/or treatment of a respiratory tract infection caused by *P. aeruginosa* in patients with cystic fibrosis.

Another embodiment provides CBD or a composition thereof for use in the prevention and/or treatment of infections caused by *P. aeruginosa* in patients with burns.

Another embodiment provides CBD or a composition thereof for use in the prevention and/or treatment of infections caused by *P. aeruginosa* in patients with chronic wounds.

In a particular embodiment, is provided a use of CBD or a composition thereof for conservation of work of art such as paintings and antique manuscripts.

In a particular embodiment, is provided a use of CBD or a composition thereof for prevention of contamination with *Pseudomonas aeruginosa* in preparations intended for human or veterinary use such as cosmetic, food, beverage or pharmaceutical preparations or for decontamination of those. In a more particular embodiment, is provided a use of CBD or a composition thereof as a sterilizing and/or decontaminating agent.

In a particular embodiment, is provided a use of CBD or a composition thereof for sterilizing and/or decontaminating medical material, rooms intended for medical, aesthetic or hygiene practice or preparations intended for human or veterinary use, in particular for decontaminating or preventing said medical material or preparations from *P. aeruginosa* contamination.

In a particular embodiment, CBD or a composition thereof is used in the context of prevention of food contamination or food decontamination.

In a particular embodiment, CBD or a composition thereof is used in the context of prevention of water contamination or water decontamination.

In a particular embodiment, CBD or a composition thereof is used in the context of prevention of contamination or for decontamination of medical material, and/or a room intended for medical, aesthetic or hygiene practice such as medical/hospital rooms, and/or clean rooms.

In a particular embodiment, CBD or compositions thereof or kits according to the invention are useful in a method according to the invention, in particular a method of inhibiting the virulence of a bacteria and/or a method of inhibiting a biofilm formation and/or a method for preventing and/or treating of a disease caused by *Pseudomonas aeruginosa* selected from the group consisting of hospital-acquired infection, respiratory tract infections, skin and soft tissue infections or diseases, chronic wound infection, chronic wound infection, urinary tract infections, ear infections, eye infections, bacteremia, sepsis, central nervous system infections and endocarditis, said method comprising administering a therapeutically effective amount of CBD, or a composition thereof, to a subject in need thereof.

In a particular embodiment, is provided a method for conservation of work of art, such as paintings and antique manuscripts, comprising the step of contacting said work of art with CBD, or a composition thereof.

In a particular embodiment, is provided a method of prevention of contamination with *Pseudomonas aeruginosa*/preservation of preparations intended for human or veterinary use such as food preparations, beverages, culture or solubilizing media, cosmetic or pharmaceutical preparations or of decontamination of those said preparations comprising a step of contacting said preparations with CBD, or a composition thereof, in particular with CBD, or a composition thereof, at a concentration between about 0.1 µg/mL to 200 mg/mL, for example from about 0.1 µg/mL to 1 mg/mL, in particular from 0.1 µg/mL to 50 µg/mL, more particularly from 1 µg/mL to 50 µg/mL.

In a particular embodiment, is provided a method of preservation or decontamination of food or meal preparation.

In a particular embodiment, is provided a method of preservation or decontamination of beverages or water.

In a particular embodiment, is provided a method of prevention of contamination with *Pseudomonas aeruginosa* of material or rooms intended for human or veterinary such as medical material or of decontamination/sterilization of those, said method comprising a step of contacting said preparations with CBD, or a composition thereof, in particular with CBD, or a composition thereof, at a concentration between about 0.1 µg/mL to 200 mg/mL, for example from about 0.1 µg/mL to 1 mg/mL, in particular from 0.1 µg/mL to 50 µg/mL, more particularly from 1 µg/mL to 50 µg/mL.

According to a particular embodiment, CBD, or a composition thereof are particularly suitable for sterilization and/or decontamination of medical material.

According to a particular embodiment, CBD, or a composition thereof are particularly suitable for sterilisation and/or decontamination of rooms intended for medical, aesthetic or hygiene practice such as medical/hospital rooms, and/or clean rooms.

Compositions According to the Invention

Compositions or formulations according to the invention may be administered as a pharmaceutical formulation.

According to another embodiment, compositions or formulations according to the invention are decontamination compositions comprising CBD and at least one further physiologically acceptable carrier, diluent or excipient.

Pharmaceutical compositions of this invention may further comprise one or more pharmaceutically acceptable additional ingredient(s) such as alum, stabilizers, antimicrobial agents, buffers, coloring agents, flavoring agents, adjuvants, and the like.

Compositions of the invention and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. According to one aspect, compositions according to the invention are sprayable or inhalable in case of respiratory infections and solutions topically applicable in case of urinary infections.

Compositions of this invention may also be liquid formulations including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agent include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the stratum corneum, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the stratum corneum.

The compounds of this invention can also be administered in sustained release forms or from sustained release drug delivery systems. A description of representative sustained release materials can also be found in the incorporated materials in *Remington's Pharmaceutical Sciences*.

Alternatively, compositions of this invention may also be formulated as an aerosolable solution or an inhalable pharmaceutically acceptable composition, e.g. suitable for prevention and/or treatment of pulmonary bacterial infections caused by gram-negative bacteria. In such a formulation, CBD is prepared for example as an inhalable dry powder or as an aerosolable solution.

The compositions according to the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral use by injection or continuous infusion, or in the form of cream, ointment, gel, paste or powder for topical use.

According to a particular embodiment, compositions of the invention are veterinary compositions.

According to a particular embodiment, compositions of the invention are hand-washing solutions, in particular hand-washing solutions for medical personnel.

According to an aspect of the invention, formulations according to the invention may be associated with or integrated within an article, notably where time-release and/or mechanical-release of the compositions is achieved, when the article is placed on an appropriate body part or in an appropriate body cavity.

According to another aspect of the invention, CBD or a composition thereof are coated on the surface of an article, in particular an article for use in medical, aesthetic or hygiene practice or in contact with preparations intended for human or veterinary use. According to another aspect, the uses and methods according to the invention for preventing *Pseudomonas aeruginosa* infections or disorders, comprise a step of coating an apparatus and materials used in healthcare and notably intensive care and surgery (such as textile, surgical material, tubings, ventilators, etc.) by a composition comprising CBD. Typically, the composition comprising CBD is incorporated into the surface or sprayed onto the surface of the said apparatus and materials used in in healthcare, in particular intensive care and surgery. Further materials as well as formulation processing techniques and the like are set out in Part 5 of Remington's "*The Science and Practice of Pharmacy*", 22$^{nd}$ Edition, 2012, University of the Sciences in Philadelphia, Lippincott Williams & Wilkins, which is incorporated herein by reference.

Combination

According to the invention, compounds and compositions according to the invention, and pharmaceutical formulations thereof may be administered alone or in combination with at least one co-agent useful for contamination prevention or decontamination.

According to a particular aspect, co-agents according to the invention include antiseptic compound and an antibiotic.

According to the invention, the compounds and compositions according to the invention, and pharmaceutical formulations is administered simultaneously with said co-agent can be administered in the same or different composition(s) and by the same or different route(s) of administration.

Mode of Administration

Compositions of this invention may be administered in any manner including, but not limited to, orally, parenterally, transdermally, transmucosally, topically, via inhalation, via buccal or intranasal administration or intra bladder, or combinations thereof.

Parenteral administration includes, but is not limited to, intravenous, intra-arterial, intra-peritoneal, subcutaneous, intramuscular and intra-cardiac.

Compositions of this invention may also be administered topically to the skin, the ear and the eye.

Compositions of the invention may be administered systemically or locally.

Compositions according to this invention may also be administered in the form of an implant, which allows slow release of the compounds and formulations thereof as well as a slow controlled i.v. infusion.

Compositions according to the invention may be administered to a subject in need thereof as a single or as a repeated administration.

Compositions according to this invention may be administered to a subject in need thereof prior to, simultaneously or sequentially with other therapeutic regimens.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Patients

In an embodiment, patients according to the invention are subjects infected by *Pseudomonas aeruginosa* or at risk of being infected by *Pseudomonas aeruginosa.*

Predisposing factors to development *Pseudomonas aeruginosa* include impaired host immunity and previous treatment with broad-spectrum antibiotic.

In an embodiment, patients according to the invention are subjects with an altered microbiota.

In an embodiment, patients according to the invention are immunosuppressed subjects.

In another embodiment, patients according to the invention are patients suffering from or at risk of suffering from a disease selected from the group consisting of hospital-acquired infection, respiratory tract infections, skin and soft tissue infections, wound infections, dental and buccal infections, otorhinolaryngologic infections, urological and/or prostatic track infections, gastrointestinal infections, biliary tract infection, eye infections, bacteremia, sepsis, central nervous system infections and endocarditis.

In a more specific embodiment, patients according to the invention are patients suffering from or at risk of suffering from a respiratory tract infection caused by *Pseudomonas aeruginosa*, such as patients with cystic fibrosis.

In another embodiment, patients according to the invention are patients with wounds.

In another embodiment, patients according to the invention are patients with burns.

In another embodiment, patients according to the invention are patients with foreign-body implants and/or catheters or who will undergo a body implant or catheter surgery.

In an embodiment, patients according to the invention are subjects at risk of infections caused by bacteria resistant to antibiotics, which are used in the animal breeding.

Kits

According to one aspect, the invention relates to a kit for carrying out a method according to the invention.

According to another aspect of the invention, is provided a kit for decontamination, in particular for decontamination of material surfaces or preparations, comprising CBD a composition thereof according to the invention, and optionally instructions for use.

According to another further embodiment, a kit according to the invention further comprises at least one antiseptic compound.

According to another further embodiment, a kit according to the invention further comprises at least one anti-virulence factor agent.

According to another further embodiment, a kit according to the invention comprising one or more sets of containers, wherein each single use set of containers comprises: a first container comprising CBD in lyophilized form or as a liquid formulation and a second container comprising sterilized tools for decontamination.

According to a particular aspect, formulations, kits and methods of the invention can be useful in the fields of conservation of work of art, cosmetic, food or beverage preparation decontamination/preservation or medical material or rooms cleaning or decontamination.

References cited herein are hereby incorporated by reference in their entirety. The present invention is not to be limited in scope by the specific embodiments and drawings described herein, which are intended as single illustrations of individual aspects of the invention, and functionally equivalent methods and components are within the scope of the invention.

EXAMPLES

The following abbreviations refer respectively to the definitions below:

CBD (cannabidiol); CV (crystal violet); lasB (gene encoding LasB Elastase); lasI (gene encoding C12 autoinducer synthase); $OD_{600}$ (optical density measured at a wavelength of 600 nm); pqsH (gene involved in quinolone autoinducer synthesis); rhlA (gene involved in rhamnolipids synthesis); rhlI (gene encoding C4 autoinducer synthase); wt (wild type).

Example 1: Reduction of Biofilm Formation of Pseudomonas aeruginosa by CBD

The effects of CBD on P. aeruginosa biofilm formation was assessed as described below. Overnight pre-cultures of Pseudomonas aeruginosa ATCC 27853 strain were diluted to an $OD_{600}$ (optical density measured at a wavelength of 600 nm) of 0.1 in 2 ml of LB (lysogeny broth) medium into polypropylene tubes. Tubes containing bacteria and CBD at concentrations of 1.9 µg/ml, 3.9 µg/ml, 7.8 µg/ml, 15.63 µg/ml, 31.25 µg/ml, 62.5 µg/ml and 125 µg/ml were incubated for 12 h at 37° C. without shaking. Planktonic cells were removed by washing once with distilled water and biofilms were stained with crystal violet (CV, 1% in water) for 30 minutes. CV was discarded and tubes were rinsed twice with water to remove excess of dye. The stained biofilms were re-suspended in 33% acetic acid and their density was evaluated by measuring the $OD_{600}$ of the suspensions normalized for bacterial density. Measurement of biofilm formation of Pseudomonas aeruginosa ATCC 27853 in the presence of CBD showed that CBD at concentrations between 1.9 µg/ml to 31.25 µg/ml can reduce by the factor of about 2 the biofilm formation as compared to control without CBD.

At higher concentration of CBD, the inhibitory effect on biofilm formation is reduced probably due to the reduced solubility of CBD in the culture medium.

Example 2: CBD-Induced Reduction of Virulence Factors Production by Pseudomonas aeruginosa The effect of CBD on the production of elastase by P. aeruginosa, a virulence factor whose expression is directly regulated by the quorum sensing system, was assessed through the measurement of the elastase enzymatic activity.

Elastase production was measured in two bacterial strains: Pseudomonas aeruginosa PAOW1(PT5) that is a wild type (wt) and Pseudomonas aeruginosa ΔlasIΔrhlI that is a mutant for quorum sensing signaling that has reduced production/expression of elastase due to the inhibition of the quorum sensing system. 100 µl of filtered bacterial supernatant of overnight cultures (with or without 500 µg/ml of CBD, where cultures were under shaking that allows better CBD dispersion) were added to 900 µl of Elastin Congo Red (ECR) buffer (100 mM Tris, 1 mM $CaCl_2$, pH 7.5 containing 20 mg of Elastin ECR) and then incubated with shaking at 37° C. for 3 h. Insoluble ECR was removed by centrifugation and the absorption of the supernatant was measured at 495 nm and normalized according to cell density.

The enzymatic activity of the elastase produced by P. aeruginosa PAOW1(PT5) in presence of CBD showed that CBD at a concentration of 500 µg/ml can reduce by about 30% the production of elastase as compared to control values (FIG. 1). The production of elastase by P. aeruginosa ΔlasIΔrhlI is reduced by about 93% as compared to control (production of elastase by wt).

These results indicate that CBD can effectively reduce the production of at least some P. aeruginosa virulence factor involved in the quorum sensing system.

Example 3: CBD-Induced Modulation of Expression of Genes Involved in Quorum Sensing of Pseudomonas aeruginosa The effects of CBD on P. aeruginosa's quorum sensing system were assessed through the expression of genes related to quorum sensing.

Overnight pre-cultures of Pseudomonas aeruginosa PAOW1(PT5) (wt) were diluted to an $OD_{600}$ of 0.05 and grown for 6 hours at 37° C. with or without 500 µg/ml of CBD. 0.5 ml of cultures were added to 1 ml of RNA Protect bacteria solution and total RNA was isolated with RNeasy columns (Qiagen). Residual DNA was eliminated by DNase treatment using 20 units of RQ1 RNase-free DNase (promega). After removal of DNase by phenol/chloroform extraction and precipitation, 500 ng of RNA was reverse-transcribed using random hexamer primers and Improm-II reverse transcriptase (promega). 2.5 µl of 10-fold diluted cDNA were quantified by real-time PCR (qPCR) using a Sybr Select Master Mix for CFX (4472942) (Thermofisher). Primers, start in gene (bp) and amplicon size (bp) used are listed in the Table 1. Each amplification was normalized by the internal standard (oprF) value of the corresponding cDNA (complementary DNA). The results are expressed as fold increase compared to the wt cultivated without CBD. The following genes' expression has been measured: rhlI encoding C4 autoinducer synthase; rhlA that is a gene involved in rhamnolipids synthesis, lasI encoding C12 autoinducer synthase, lasB encoding LasB Elastase and pqsH that is a gene involved in quinolone autoinducer synthesis.

TABLE 1

| gene | primer | sequence | start in gene (bp) | amplicon size (bp) |
|---|---|---|---|---|
| rhlI | 309 | SEQ ID NO: 1: CTCTCTGAATCGCTGGAAGG | 13 | 240 |
| | 310 | SEQ ID NO: 2: GACGTCCTTGAGCAGGTAGG | 252 | |
| rhlA | 299 | SEQ ID NO: 3: CGAGGTCAATCACCTGGTCT | 279 | 208 |
| | 300 | SEQ ID NO: 4: GACGGTCTCGTTGAGCAGAT | 486 | |
| lasI | 311 | SEQ ID NO: 5: CTACAGCCTGCAGAACGACA | 390 | 168 |
| | 312 | SEQ ID NO: 6: ATCTGGGTCTTGGCATTGAG | 557 | |
| lasB | 301 | SEQ ID NO: 7: AAGCCATCACCGAAGTCAAG | 260 | 230 |
| | 302 | SEQ ID NO: 8: GTAGACCAGTTGGGCGATGT | 489 | |
| pqsH | 303 | SEQ ID NO: 9: ATGTCTACGCGACCCTGAAG | 629 | 169 |
| | 304 | SEQ ID NO: 10: AACTCCTCGAGGTCGTTGTG | 797 | |

Figure 2:
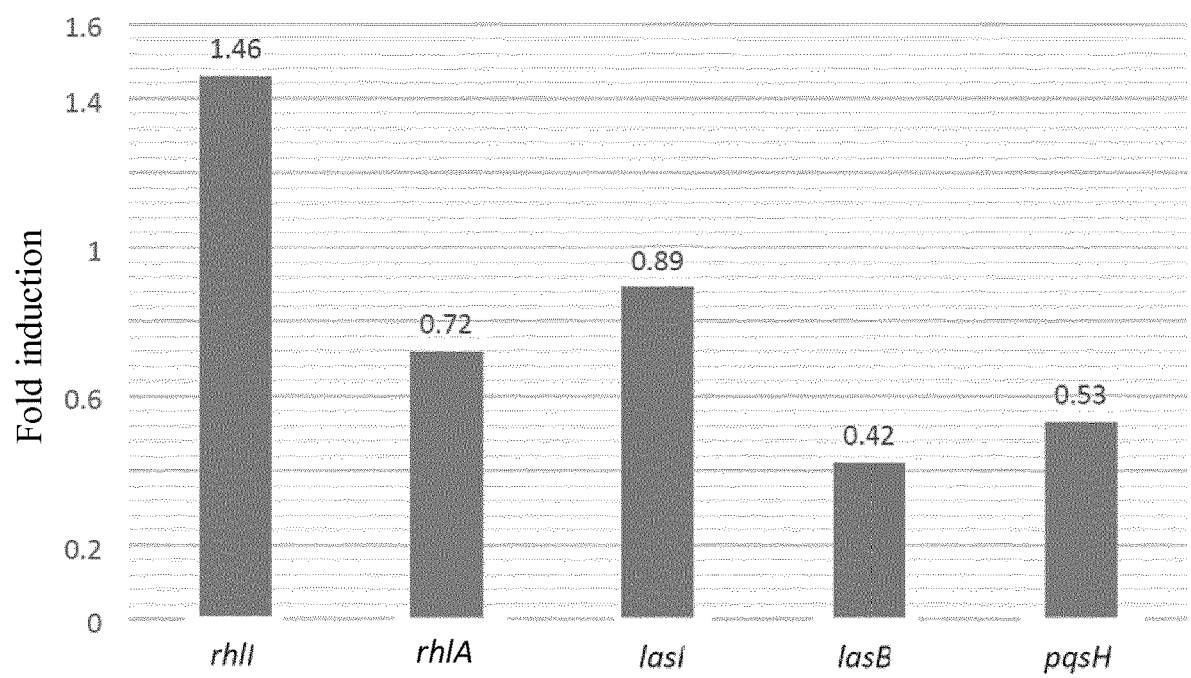
FIG. 2 shows the fold induction (FI) of the expression of genes that are related to *P. aeruginosa*'s quorum sensing system in presence of CBD as described in Example 3.

The fold induction of expression of genes by *P. aeruginosa* PAOW1(PT5) incubated in the presence of CBD (500 µg/ml) was 1.46 for rhlI, 0.72 for rhl A, 0.89 for lasI, 0.42 lasB and 0.53 for pqsH as compared to control conditions (FIG. 2) which indicates that CBD is able to affect the *Pseudomonas aeruginosa* virulence by interfering with the quorum sensing system.

| Sequence listing | |
|---|---|
| Nucleic acid sequence of rhlI primer 309 SEQ ID NO: 1: CTCTCTGAATCGCTGGAAGG | |
| Nucleic acid sequence of rhlI primer 310 SEQ ID NO: 2: GACGTCCTTGAGCAGGTAGG | |
| Nucleic acid sequence of rhlA primer 299 SEQ ID NO: 3: CGAGGTCAATCACCTGGTCT | |
| Nucleic acid sequence of rhlA primer 300 SEQ ID NO: 4: GACGGTCTCGTTGAGCAGAT | |

-continued

| Sequence listing | |
|---|---|
| Nucleic acid sequence of lasI primer 311 SEQ ID NO: 5: CTACAGCCTGCAGAACGACA | |
| Nucleic acid sequence of lasI primer 312 SEQ ID NO: 6: ATCTGGGTCTTGGCATTGAG | |
| Nucleic acid sequence of lasB primer 301 SEQ ID NO: 7: AAGCCATCACCGAAGTCAAG | |
| Nucleic acid sequence of lasB primer 302 SEQ ID NO: 8: GTAGACCAGTTGGGCGATGT | |
| Nucleic acid sequence of pqsH primer 303 SEQ ID NO: 9: ATGTCTACGCGACCCTGAAG | |
| Nucleic acid sequence of pqsH primer 304 SEQ ID NO: 10: AACTCCTCGAGGTCGTTGTG | |

The invention claimed is:

1. A method for treating a disease caused by *P. aeruginosa* bacteria, said method comprising administering a therapeutically effective amount of CBD, or a composition thereof, to a subject in need thereof, wherein said disease caused by *P. aeruginosa* bacteria is selected from the group consisting of hospital-acquired infection, respiratory tract infections, skin and soft tissue infections, wound infections, dental and buccal infections, otorhinolaryngologic infections, urological and/or prostatic track infections, gastrointestinal infections, biliary tract infection, eye infections, bacteremia, sepsis, central nervous system infections and endocarditis.

2. The method according to claim 1, wherein said disease caused by *P. aeruginosa* bacteria is an otorhinolaryngologic infection.

3. The method according to claim 1, wherein said disease caused by *P. aeruginosa* bacteria is a skin and soft tissue infection.

4. The method according to claim 1, wherein said disease caused by *P. aeruginosa* bacteria is a wound infection.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Nucleic acid sequence of rhlI primer 309

<400> SEQUENCE: 1
ctctctgaat cgctggaagg                                          20

<210> SEQ ID NO 2
<211> LENGTH: 20
<212> TYPE: DNA
<213> ORGANISM: Artificial Sequence
<220> FEATURE:
<223> OTHER INFORMATION: Nucleic acid sequence of rhlI primer 310

<400> SEQUENCE: 2
gacgtccttg agcaggtagg                                          20

<210> SEQ ID NO 3
<211> LENGTH: 20

-continued

```
<212> TYPE: DNA
<213> ORGANISM: Artificial Sequence
<220> FEATURE:
<223> OTHER INFORMATION: Nucleic acid sequence of rhlA primer 299

<400> SEQUENCE: 3
cgaggtcaat cacctggtct                                               20

<210> SEQ ID NO 4
<211> LENGTH: 20
<212> TYPE: DNA
<213> ORGANISM: Artificial Sequence
<220> FEATURE:
<223> OTHER INFORMATION: Nucleic acid sequence of rhlA primer 300

<400> SEQUENCE: 4
gacggtctcg ttgagcagat                                               20

<210> SEQ ID NO 5
<211> LENGTH: 20
<212> TYPE: DNA
<213> ORGANISM: Artificial Sequence
<220> FEATURE:
<223> OTHER INFORMATION: Nucleic acid sequence of lasI primer 311

<400> SEQUENCE: 5
ctacagcctg cagaacgaca                                               20

<210> SEQ ID NO 6
<211> LENGTH: 20
<212> TYPE: DNA
<213> ORGANISM: Artificial Sequence
<220> FEATURE:
<223> OTHER INFORMATION: Nucleic acid sequence of lasI primer 312

<400> SEQUENCE: 6
atctgggtct tggcattgag                                               20

<210> SEQ ID NO 7
<211> LENGTH: 20
<212> TYPE: DNA
<213> ORGANISM: Artificial Sequence
<220> FEATURE:
<223> OTHER INFORMATION: Nucleic acid sequence of lasB primer 301

<400> SEQUENCE: 7
aagccatcac cgaagtcaag                                               20

<210> SEQ ID NO 8
<211> LENGTH: 20
<212> TYPE: DNA
<213> ORGANISM: Artificial Sequence
<220> FEATURE:
<223> OTHER INFORMATION: Nucleic acid sequence of lasB primer 302

<400> SEQUENCE: 8
gtagaccagt tgggcgatgt                                               20

<210> SEQ ID NO 9
<211> LENGTH: 20
<212> TYPE: DNA
<213> ORGANISM: Artificial Sequence
<220> FEATURE:
<223> OTHER INFORMATION: Nucleic acid sequence of pqsH primer 303

<400> SEQUENCE: 9
```

-continued

```
atgtctacgc gaccctgaag                                             20

<210> SEQ ID NO 10
<211> LENGTH: 20
<212> TYPE: DNA
<213> ORGANISM: Artificial Sequence
<220> FEATURE:
<223> OTHER INFORMATION: Nucleic acid sequence of pqsH primer 304

<400> SEQUENCE: 10
aactcctcga ggtcgttgtg                                             20
```